US005324522A

United States Patent [19]

Krenning et al.

[11] Patent Number: 5,324,522
[45] Date of Patent: Jun. 28, 1994

[54] SUSTAINED RELEASE THYROACTIVE COMPOSITION

[75] Inventors: Eric P. Krenning; Georg Hennemann, both of Rotterdam, Netherlands

[73] Assignee: Akzo N.V., Arnhem, Netherlands

[21] Appl. No.: 997,474

[22] Filed: Dec. 28, 1992

[30] Foreign Application Priority Data

Dec. 30, 1991 [EP] European Pat. Off. ......... 91203438

[51] Int. Cl.$^5$ ............................................. A61K 9/64
[52] U.S. Cl. ................................. 424/456; 424/426; 424/464; 424/475; 424/473; 424/482
[58] Field of Search ............... 562/447, 464, 424, 447; 424/426, 475, 482, 456; 514/567

[56] References Cited

U.S. PATENT DOCUMENTS

| | | | |
|---|---|---|---|
| 3,065,143 | 11/1962 | Christenson et al. | 424/468 |
| 3,344,029 | 9/1967 | Berger | 424/470 |
| 3,410,891 | 11/1968 | Hughes | 562/447 |
| 3,477,954 | 11/1969 | Reynolds | 562/447 |
| 3,577,535 | 5/1971 | Reynolds et al. | 514/75 |
| 3,689,669 | 9/1972 | Prange et al. | 514/567 |
| 3,928,553 | 12/1975 | Hollander | 436/500 |
| 3,939,259 | 2/1976 | Pescetti | 424/460 |
| 4,012,498 | 3/1977 | Kornblum et al. | 424/470 |
| 4,357,469 | 11/1982 | Schor | 536/91 |
| 4,369,172 | 6/1983 | Schor et al. | 424/468 |
| 4,389,393 | 6/1983 | Schor et al. | 424/469 |
| 4,666,702 | 5/1987 | Junginger | 424/497 |
| 4,680,323 | 7/1987 | Lowey | 424/435 |
| 4,851,232 | 7/1989 | Urquhart et al. | 424/469 |
| 4,915,954 | 4/1990 | Ayer et al. | 424/473 |
| 4,970,075 | 11/1990 | Oshlack | 424/451 |

FOREIGN PATENT DOCUMENTS

| | | |
|---|---|---|
| 0384514A | 8/1990 | European Pat. Off. . |
| 0396425A | 11/1990 | European Pat. Off. . |
| 2191695 | 12/1987 | United Kingdom . |
| 219206 | 12/1989 | United Kingdom . |

OTHER PUBLICATIONS

*Remingtons Pharmaceutical Sciences* (18th Edition), Mack Publishing Co., Easton, PA, USA (1990), pp. 979–981 and 1676–1693.

*Primary Examiner*—Thurman K. Page
*Assistant Examiner*—W. Benston
*Attorney, Agent, or Firm*—William M. Blackstone; Mary E. Gormley

[57] ABSTRACT

Disclosed are sustained release dosage forms of liothyronine, in combination with normal or sustained release of thyroxine in a molar ratio of about 1 to 50:1, especially 5 to 20:1, useful in thyroid hormone replacement therapy. Surprisingly, it is found that by incorporating liothyronine and optionally thyroxine into a prolonged action dosage form in the described ratios, that the side effects associated with thyroid hormone replacement therapy are greatly reduced or eliminated. The preparation can be a dosage form containing salts of both thyroxine and liothyronine which release in a sustained manner. The preparations will typically contain 5 to 25 μg of liothryronine. Also disclosed are processes of manufacturing the pharmaceutical preparations. The compositions are useful in treating disease states such as hypothyroidism, hyperthyroidism (in combination with thyrostatic drugs), so-called "TSH" suppressive therapy, and depression.

8 Claims, No Drawings

SUSTAINED RELEASE THYROACTIVE COMPOSITION

TECHNICAL FIELD

The invention relates to pharmaceutical preparations generally, and more specifically to a preparation useful in replacement therapy for thyroactive material normally supplied by the thyroid gland.

BACKGROUND ART

The thyroid gland, among other things, modulates a body's energy metabolism. It does so by releasing various iodinated thyronines. Two of these iodinated thyronines are thyroxine (3,5,3',5'-tetraiodothyronine or "T-4") and liothyronine (3,5,3'-triiodothyronine or "T-3").

Various diseases affecting the thyroid or pituitary gland can result in hypothyroidism. Hypothyroidism can also result from thyroid surgery or treatment with radioactive iodine. In a "hypothyroid" state, the body's basal metabolic state drops, and growth and development may be impaired.

Hypothyroidism is usually treated by administering exogenous "thyroid hormone" (actually a combination of thyroxine and liothyronine) or levothyroxine or liothyronine alone.

Other treatments include administering combination dosage forms containing a 4:1 mixture of levothyroxine to liothyronine. Such combination dosage forms are commonly called "liotrix tablets" and are available under the trademark names "Euthroid" (Parke-Davis) and "Thyrolar" (Rorer). Such tablets typically contain 25 µg:6.25 µg, 30 µg:7.5 µg, 50 µg:12.5 µg, 60 µg:15 µg, 100 µg:25 µg, 150 µg:37.5 µg, or 180 µg:45 µg (levothyroxine: liothyronine).

This 4 to 1 ratio of T-4 to T-3 is carried forward pretty much consistently in the patent literature. For example, U.S. Pat. Nos. 3,577,535 and 3,477,954 broadly disclose ratios varying from 2.3:1 (EXAMPLE I) to 8:1 (EXAMPLE III), but 4:1 is still seen as ideal. WO 91/06569 discloses a iodothyronine polymer which may have sustained release properties, but the 4 to 1 ratio is still preferred even though the disclosed ratios do vary from 70 to 90% T-4 with 10 to 30% T-3.

Treatment of hypothyroidism even with these combination preparations can still result in undesirable side effects, such as angina, palpitations, an increased incidence of osteoporosis, and hypertension.

Furthermore, with tablets containing only T-4, if a higher than normal thyroxine to liothyronine plasma level results, subnormal TSH levels appear, apparently due to the pituitary being in a state of thyrotoxicosis. This thyrotoxicosis may also affect other organs and systems of the body.

DISCLOSURE OF THE INVENTION

Surprisingly it is found that by incorporating liothyronine into a sustained or prolonged release dosage form, and co-administering it along with thyroxine (preferably also in a sustained or prolonged release form) in a preselected ratio, that the side effects generally associated with thyroid hormone replacement therapy are greatly reduced or eliminated. Furthermore, the dosage of liothyronine administered is generally lower than with earlier treatment regimens.

The invention thus includes a pharmaceutical preparation useful in thyroid hormone replacement therapy comprising a sustained release form of liothyronine in combination with thyroxine. Such preparations will contain therapeutically useful amounts of liothyronine.

The invention also includes pharmaceutical preparations containing both liothyronine and thyroxine, having a controlled release of liothyronine and either a controlled or normal release of thyroxine.

The preparation can be a single unit dosage form containing salts of both thyroxine and liothyronine in a molar ratio of about 10:1 (in a broad molar ratio of 1 to 50:1, and preferably of 5 to 20:1), when the levo-rotatory isomers of the compounds are used. The liothyronine is in the unit dosage form in a slow release form, while the thyroxine may, but need not, release normally. The dosage form is formulated so that the liothyronine and thyroxine release from the dosage form in such a manner that, taking into consideration their relative rates of metabolism, they mimic physiological levels of these hormones.

The invention also includes processes of manufacturing the pharmaceutical preparations.

Once made, the compositions of the invention are useful in treating disease states which are susceptible to treatment by thyroid hormone generally. Such disease states include hypothyroidism, hyperthyroidism (in combination with anti-thyroid drugs, such as methimazol, propylthiouracil, or carbimazole), so called "TSH" suppresslye therapy, and depression.

It is found that the use of the preparation boosts the physiological thyroid hormone and thyroid stimulating hormone (TSH) levels in a more natural manner, therefore decreasing the chance of local thyrotoxicosis or hypothyroidism in organs. It is further found that TSH level is elevated in comparison with conventional release regimens. It further decreases the confusion seen with interpreting serum thyroid hormone levels of subjects undergoing hormone replacement therapy, since the resulting thyroid hormone blood levels are similar to that seen in the "normal" population.

BEST MODE OF THE INVENTION

The levorotatory isomers of the thyroid hormones are highly preferred for use in the invention. Levothyroxine and liothyronine are both commercially available. The compounds can also be either derived from thyroid glands or prepared by chemical synthesis. See, e.g. the well-known text Stewart C. Harvey et al., *Remington's Pharmaceutical Sciences*, (18th ed., Mack Publishing Co., Easton. PA, U.S.A., 1990) ("*Remington's*"), at pages 979 to 981. The monosodium salts of these compounds are preferred, although other, especially Group IA (e.g. potassium), element salts may also be useful.

The dose of liothyronine and thyroxine in the pharmaceutical preparations of the invention are preferably chosen with a particular patient in mind. However, pharmaceutical preparations made according to the invention containing sufficient T-3 and T-4 to provide a daily dosage of 5 to 25, preferably 10–18 µg (e.g. 13 µg) of T-3 and 25 to 200 µg, preferably 80–140 µg (e.g. 110 µg), of T-4 are extremely useful in the practice of the invention. The ultimate dosage to provide physiological thyroid hormone substitution depends, apart from individual characteristics, on the degree of residual thyroid function, the gastrointestinal absorption of the preparation, the patient's weight, and age.

Furthermore, the amount of T-3 or T-4 contained within a pharmaceutical preparation will also depend on the amount of drug which actually releases from the preparation into the gastrointestinal tract. This consideration is especially important for sustained or prolonged release preparations presently available, especially ones in which the entire amounts of the drug are not released into the patient's system.

The pharmaceutical preparation will preferably be an oral dosage unit, e.g. a tablet or capsule, containing and releasing the described doses of both T-3 and T-4 in a prolonged or sustained-release manner. Methods and dosage units useful for adaptation to make such sustained-release or prolonged release dosage units are well-known to those skilled in the art.

However, tablets or capsules having a biphasic release profile with the T-4 having a normal release and the T-3 having a prolonged release are also useful for the practice of the invention. Preparations useful for the practice of the invention in such a manner can be the so-called "dual-action" tablets such as those described in European patent application 384 514 A (corresponding to U.S. Ser. No. 314,672 filed Feb. 21, 1989); an osmotic device, such as that described in U.S. Pat. No. 4,915,954; dosage units such as those described in U.S. Pat. No. 4,666,702; or compositions such as those disclosed in EP 396,425 A.

Other dual-action dosage forms include relatively small prolonged-release pellets of T-3 imbedded in a T-4 containing matrix. The matrix being of a standard release composition. The resulting mixture can then be tabletted or incorporated into a capsule. Once such a dosage form is ingested the T-4 containing matrix would dissolve, freeing the small prolonged-release pellets of T-3 for a slow release of this hormone.

The T-3 and T-4 or either of them are preferably incorporated into dosage units for oral administration. The term "dosage unit" generally refers to physically discrete units suitable as unitary dosages for humans or animals (e.g. tablets and capsules), each containing a predetermined quantity of active material (e.g. T-3 or T-4) calculated to produce the desired effect.

The amount of T-3 and T-4 in a dosage unit will depend somewhat on the length of time the prolonged release dosage form releases T-3 and T-4 remains in the subject's system. Ideally the release time will be such so as to avoid any significant change in serum T-3 or T-4 levels after steady state has been reached. Preferably the T-3 and T-4 will release over a 12 to 24 hour period. The 24 hour period is especially preferred to allow for an optimal once a day dosing. In such a case 13 $\mu$g of T-3 and 110 $\mu$g of T-4 will typically be used for a 70 kilogram person. However, due to the passage of the dosage unit from the patient's system, a 12 hour (twice a day) dosing schedule might be more common using tablets releasing 7 $\mu$g of T-3 and 55 $\mu$g of T-4 which release in a sustained-release manner. Furthermore however, even shorter (e.g. 6 to 8 hours) periods of sustained release are useful. With shorter schedules, multiple daily dosing is preferred.

"Sustained release", "prolonged release", and "prolonged action" are terms well known to those skilled in the art. See, e.g. *Remington's* at pages 1676 to 1693 Other related terms include "controlled release". See, e.g. U.S. Pat. No. 4,666,702.

Methods and compositions for making dosage units useful for practicing the invention are well-known to those skilled in the art. For example, besides the herein referenced patent publications disclosing "dual action" dosage units, methods and compositions for making prolonged-action pharmaceuticals are described *Remington's* at pages 1682 through 1693. Methods of coating pharmaceutical dosage forms are described at pages 1666 to 1675 of Remington's.

For making dosage units, e.g. tablets, the use of conventional additives, e.g. fillers, colorants, polymeric binders and the like is contemplated. In general any pharmaceutically acceptable additive which does not interfere with the function of the active compounds can be used in the one or more of the compositions.

Suitable carriers with which the compositions can be administered include lactose, starch, cellulose derivatives and the like used in suitable amounts. Mixtures of carriers can also be used.

Other sustained release dosage forms which may be used with the invention include those described in the following patent documents: U.S. Pat. No. 4,851,232, U.S. Pat. No. 4,970,075, GB 2,219,206, U.S. Pat. No. 4,680,323, U.S. Pat. No. 4,357,469, U.S. Pat. No. 4,369,172, U.S. Pat. No. 4,389,393, U.S. Pat. No. 3,344,029, U.S. Pat. No. 4,012,498, U.S. Pat. No. 3,939,259, and U.S. Pat. No. 3,065,143, the contents of all of which are incorporated by this reference.

A process of manufacturing the pharmaceutical product according to the invention preferably involves incorporating the desired dosages of the T-3 or T-4 into a dosage unit (e.g. tablet) by adapting known techniques. Tablets containing the T-3, T-4 or mixtures thereof may first be made then kept in a blister pack. Capsules containing prolonged-release pellets of T-3 and T-4 can be mixed with a filler and capsules made by enclosing the desired dosages into a gelatin capsule.

A method of providing thyroid hormone replacement therapy using the pharmaceutical preparation of the instant invention comprises administering the described pharmaceutical preparation to a person in need thereof. The treatment may be continued for as long as desired. It is especially preferred to monitor the patient's serum thyroid stimulating hormone levels to determine if the amount of thyroid hormone being supplied by the therapy is adequate, too much or too little.

In one embodiment, slow-release tablets containing only the desired amount of T-3 are co-administered with sustained or normal release tablets containing T-4. However, a sustained release preparation (dosage unit) containing both T-3 and T-4 is preferred, since, among other things, it is generally less expensive, and more "patient friendly" thus allowing for better patient compliance, since only a single dosage unit need be taken once or twice daily.

While not intending to be bound by one theory of the invention, the following may help explain the benefits achieved with the inventive combination over the prior art combinations. The ratio of T-4 to T-3 in the prior art combinations is unphysiological in that it is based on the misconception that total T-4/T-3 production in man occurs independently from each other. Above normal peak T-3 serum levels thus result due to the unphysiological T-3/T-4 ratio in the prior art therapy. Such supernormal levels may result in undesired side effects.

With the present invention however, peak levels of T-3 and T-4 are attenuated, due to the decreased total amount of T-3 and sustained release of T-3 and/or T-4 from the preparation, thus resulting in fewer of the side effects commonly seen with administration of the prior art exogenous thyroid hormone. Furthermore, with the inventive preparations, the ratio of serum T-3 to T-4 actually reaching the systemic circulation more closely mimics levels seen in a euthyroid individual.

The invention is further explained by the following illustrative EXAMPLES.

EXAMPLE I

Controlled Release Tablets

Tablets having a hydrophillic swellable matrix system are made containing:

| Compound | Amount (mg/tablet) |
| --- | --- |
| T-3 Na | 0.003 |
| T-4 Na | 0.075 |
| hydroxypropylmethylcellulose | 80.0 |
| sodium carboxymethylcellulose | 40.0 |
| calcium phosphate | 78.88 |
| magnesium stearate | 1.12 |
| total mass | 200.1 mg |

The tablets release T-3 and T-4 over a period of 1.5 to 24 hours.

EXAMPLE II

Controlled Release T-3 & T-4 Tablets

Again as described in U.S. Pat. No. 4,666,702, substituting T-3 and T-4 for the described active ingredients, are made tablets containing:

| Compound | Amount (mg/tablet) |
| --- | --- |
| T-3 | 0.003 |
| T-4 | 0.075 |
| mannitol | 10.000 |
| magnesium stearate | 0.065 |
| calcium phosphate | qsad 100.000 |

These "core" tablets, once made, are mixed with microporous polypropylene having a void space of 75% (Accurel P.P.) and are compressed (compression force 300 kg per cm$^2$) into coated tablets. The coated tablet is designed to release T-3 and T-4 at a constant rate about 4 hours after oral administration.

EXAMPLE III

Osmotic Delivery Device

Into the device described in U.S. Pat. No. 4,915,954, are incorporated T-3 and T-4. 150 μg (per osmotic delivery device) of T-4 are incorporated into composition (A) along with hydroxypropyl cellulose. T-4 thus releases over 1 to 120 minutes. 6 μg (per osmotic delivery device) of T-3 are incorporated into composition (B) along with hydroxypropylmethylcellulose- T-3 thus releases over 1.5 to 24 hours.

EXAMPLE IV

Controlled Release T-3 Tablets

As described in U.S. Pat. No. 4,666,702, substituting T-3 for the described active ingredients, are made tablets containing:

| Compound | Amount (mg/tablet) |
| --- | --- |
| T-3 | 0.006 |
| corn starch | 10.000 |
| cellulose | 0.100 |
| magnesium stearate | 0.065 |
| calcium phosphate | qsad 100.000 |

These "core" tablets, once made, are mixed with microporous polypropylene having a void space of 75% (Accurel P.P.) and are compressed (compression force 300 kg per cm$^2$) into coated tablets. The coated tablet is designed to release T-3 at a constant rate about 4 hours after oral administration. These tablets are intended to be co-administered with tablets containing appropriate amounts of T-4 only (e.g. Thyrax ™ by Organon Nederland, bv - Oss, NL).

EXAMPLE V

Controlled Release T-3 Tablets

A solution of T-3 in ethanol is applied on dicalcium phosphate, dried, mixed with the described ingredients and compressed to obtain tablets containing:

| Compound | Amount (mg/tablet) |
| --- | --- |
| T-3 | 0.005 |
| Methocel K100M (intra-granular) | 16.125 |
| dicalc. phosphate 2 aq. | 181.670 |
| Methocel K100M (inter-granular) | 16.125 |
| magnesium stearate | 1.075 |
| Total mass tablet | 215 mg |

Reference herein to specific embodiments or examples should not be interpreted as limitations to the scope of the invention, which is defined by the appended claims.

What is claimed is:

1. A pharmaceutical composition for thyroid hormone replacement therapy comprising thyroxine and a controlled release form of 3,5,3'-triiodothyronine, said preparation containing from 1 to 50 parts of thyroxine to one part of 3,5,3'-triiodothyronine or pharmaceutically acceptable salts thereof.

2. The pharmaceutical composition of claim 1, which releases therefrom 5 to 25 μg of 3,5,3'-triiodothyronine.

3. The pharmaceutical composition of claim 2, wherein the thyroxine is levo-thyroxine in a form that releases in a controlled manner from said pharmaceutical composition.

4. The pharmaceutical composition of claim 2, wherein the 3,5,3'-triiodothyronine releases over a 1.5 to 24 hour period.

5. A pharmaceutical composition according to claim 1, comprising from 1 to 50 parts of thyroxine to one part of 3,5,3'-triiodothyronine, which releases thyroxine and 3,5,3'-triiodothyronine in a controlled release manner over a period of 1.5 to 24 hour.

6. A pharmaceutical composition according to claim 1, comprising salts of both levo-thyroxine and 3,5,3'-triiodothyronine that are released in a molar ratio of about 1:1 to 50:1, respectively, and at least the 3,5,3'-triiodothyronine is in said preparation in a controlled release form.

7. A pharmaceutical dosage unit comprising levo-thyroxine and 3,5,3'-triiodothyronine, wherein the dosage unit releases from 25 to 200 μg of levothyroxine, and further releases, in a controlled manner, from 5 to 25 μg of 3,5,3'-triidothyronine, said levothyroxine and 3,5,3'-triiodothyronine being released, in total, in a molar ratio of about 1:1 to 50:1.

8. A method of hormone replacement therapy comprising administering a pharmaceutical composition comprising 3,5,3'-triiodothyronine which releases, over a twelve hour period, 5 to 25 μg of 3,5,3'-triiodothyronine.

* * * * *